US010582983B2

(12) United States Patent
Roll Hoye

(10) Patent No.: US 10,582,983 B2
(45) Date of Patent: Mar. 10, 2020

(54) ULTRASONIC ENDOVASCULAR CATHETER WITH A CONTROLLABLE SHEATH

(71) Applicant: C.R. Bard, Inc., Tempe, AZ (US)

(72) Inventor: Jessica Lynn Roll Hoye, Phoenix, AZ (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 270 days.

(21) Appl. No.: 15/425,321

(22) Filed: Feb. 6, 2017

(65) Prior Publication Data

US 2018/0221040 A1  Aug. 9, 2018

(51) Int. Cl.
*A61B 90/00* (2016.01)
*A61B 17/22* (2006.01)

(52) U.S. Cl.
CPC ........ *A61B 90/39* (2016.02); *A61B 17/22012* (2013.01); *A61B 2017/22014* (2013.01); *A61B 2017/22094* (2013.01); *A61B 2090/0811* (2016.02); *A61B 2090/3937* (2016.02); *A61B 2090/3966* (2016.02)

(58) Field of Classification Search
CPC .............. A61B 90/39; A61B 17/22012; A61B 2017/22014; A61B 2017/22094; A61B 2090/3937; A61B 2090/0811; A61B 2090/3966
USPC .................................................. 600/437–469
See application file for complete search history.

(56) References Cited

U.S. PATENT DOCUMENTS

| | | |
|---|---|---|
| 3,296,620 A | 1/1967 | Rodda |
| 3,433,226 A | 3/1969 | Boyd |
| 3,443,226 A | 5/1969 | Knight |
| 3,565,062 A | 2/1971 | Kurls |
| 3,585,082 A | 6/1971 | Siller |
| 3,612,038 A | 10/1971 | Halligan |
| 3,631,848 A | 1/1972 | Muller |
| 3,679,378 A | 7/1972 | Van Impe et al. |
| 3,719,737 A | 3/1973 | Vaillancourt et al. |
| 3,739,460 A | 6/1973 | Addis et al. |
| 3,754,746 A | 8/1973 | Thiele |

(Continued)

FOREIGN PATENT DOCUMENTS

| | | |
|---|---|---|
| AU | 2007240154 A1 | 1/2008 |
| DE | 2256127 A1 | 5/1974 |

(Continued)

OTHER PUBLICATIONS

Noone, D.: Experimental and Numerical Investigation of Wire Waveguides for Therapeutic Ultrasound Angioplasty. M.Eng. Dublin City University. 2008.

(Continued)

*Primary Examiner* — Sanjay Cattungal

(57) ABSTRACT

An apparatus for performing an endovascular procedure using ultrasonic energy includes a catheter with a proximal end portion and a distal end portion. The distal end portion includes a first window, which may expose a wave guide for delivering the ultrasonic energy for performing the endovascular procedure. A cover may be provided for selectively covering the window. By selectively controlling the position of the sheath, the transmission of ultrasonic energy may be regulated accordingly for providing a desired treatment regimen.

14 Claims, 3 Drawing Sheets

(56) References Cited

U.S. PATENT DOCUMENTS

| | | |
|---|---|---|
| 3,823,717 A | 7/1974 | Pohlman et al. |
| 3,835,690 A | 9/1974 | Leonhardt et al. |
| 3,839,841 A | 10/1974 | Amplatz |
| 3,896,811 A | 7/1975 | Storz |
| 4,016,882 A | 4/1977 | Broadwin et al. |
| 4,033,331 A | 7/1977 | Guss et al. |
| 4,136,700 A | 1/1979 | Broadwin et al. |
| 4,337,090 A | 6/1982 | Harrison |
| 4,368,410 A | 1/1983 | Hance et al. |
| 4,417,578 A | 11/1983 | Banko |
| 4,425,115 A | 1/1984 | Wuchinich |
| 4,449,523 A | 5/1984 | Szachowicz et al. |
| 4,453,935 A | 6/1984 | Newton |
| 4,486,680 A | 12/1984 | Bonnet et al. |
| 4,505,767 A | 3/1985 | Quin |
| 4,535,759 A | 8/1985 | Polk et al. |
| 4,545,767 A | 10/1985 | Suzuki et al. |
| 4,565,589 A | 1/1986 | Harrison |
| 4,565,787 A | 1/1986 | Bossle et al. |
| 4,572,184 A | 2/1986 | Stohl et al. |
| 4,664,112 A | 5/1987 | Kensey et al. |
| 4,665,906 A | 5/1987 | Jervis |
| 4,679,558 A | 7/1987 | Kensey et al. |
| 4,700,705 A | 10/1987 | Kensey et al. |
| 4,721,117 A | 1/1988 | Mar et al. |
| 4,750,902 A | 6/1988 | Inuchinich et al. |
| 4,781,186 A * | 11/1988 | Simpson .......... A61B 17/22031 604/913 |
| 4,808,153 A | 2/1989 | Parisi |
| 4,811,743 A | 3/1989 | Stevens |
| 4,827,911 A | 5/1989 | Broadwin et al. |
| 4,838,853 A | 6/1989 | Parisi |
| 4,854,325 A | 8/1989 | Stevens |
| 4,870,953 A | 10/1989 | DonMicheal et al. |
| 4,886,060 A | 12/1989 | Wiksell |
| 4,920,954 A | 5/1990 | Alliger et al. |
| 4,923,462 A | 5/1990 | Stevens |
| 4,924,863 A | 5/1990 | Sterzer |
| 4,931,047 A | 6/1990 | Broadwin et al. |
| 4,936,281 A | 6/1990 | Stasz |
| 4,936,845 A | 6/1990 | Stevens |
| 4,979,952 A | 12/1990 | Kubota et al. |
| 5,000,185 A | 3/1991 | Yock |
| 5,015,227 A | 5/1991 | Broadwin et al. |
| 5,026,384 A | 6/1991 | Farr et al. |
| 5,030,201 A | 7/1991 | Palestrant |
| 5,030,357 A | 7/1991 | Lowe |
| 5,046,503 A | 9/1991 | Schneiderman |
| 5,053,008 A | 10/1991 | Bajaj |
| 5,058,570 A | 10/1991 | Idemoto et al. |
| 5,076,276 A | 12/1991 | Sakurai et al. |
| 5,091,205 A | 2/1992 | Fan |
| 5,100,423 A | 3/1992 | Fearnot |
| 5,109,859 A | 5/1992 | Jenkins |
| 5,114,414 A | 5/1992 | Buchbinder |
| 5,116,350 A | 5/1992 | Stevens |
| 5,127,917 A | 7/1992 | Niederhauser et al. |
| 5,131,393 A | 7/1992 | Ishiguro et al. |
| 5,156,143 A | 10/1992 | Bocquet et al. |
| 5,163,421 A | 11/1992 | Bernstein et al. |
| 5,171,216 A | 12/1992 | Dasse et al. |
| 5,180,363 A | 1/1993 | Idemoto et al. |
| 5,183,470 A | 2/1993 | Wettermann |
| 5,195,955 A | 3/1993 | Don Michael |
| 5,215,614 A | 6/1993 | Wijkamp et al. |
| 5,217,565 A | 6/1993 | Kou et al. |
| 5,221,255 A | 6/1993 | Mahurkar et al. |
| 5,226,421 A | 7/1993 | Frisbie et al. |
| 5,234,416 A | 8/1993 | Macaulay et al. |
| 5,236,414 A * | 8/1993 | Takasu .............. A61B 17/22012 601/3 |
| 5,238,004 A | 8/1993 | Sahatjian et al. |
| 5,242,385 A | 9/1993 | Strukel |
| 5,243,997 A | 9/1993 | Uflacker et al. |
| 5,248,296 A | 9/1993 | Alliger |
| 5,255,669 A | 10/1993 | Kubota et al. |
| 5,267,954 A | 12/1993 | Nita |
| 5,269,291 A | 12/1993 | Carter |
| 5,269,297 A | 12/1993 | Weng et al. |
| 5,269,793 A | 12/1993 | Simpson |
| 5,279,546 A | 1/1994 | Mische et al. |
| 5,287,858 A | 2/1994 | Hammerslag et al. |
| 5,290,229 A | 3/1994 | Paskar |
| 5,304,115 A | 4/1994 | Pflueger et al. |
| 5,304,131 A | 4/1994 | Paskar |
| 5,312,328 A | 5/1994 | Nita et al. |
| 5,318,014 A | 6/1994 | Carter |
| 5,318,570 A | 6/1994 | Hood et al. |
| 5,324,255 A | 6/1994 | Passafaro et al. |
| 5,324,260 A | 6/1994 | O'Neill et al. |
| 5,325,860 A | 7/1994 | Seward et al. |
| 5,326,342 A | 7/1994 | Pflueger et al. |
| 5,328,004 A | 7/1994 | Fannin et al. |
| 5,329,927 A | 7/1994 | Gardineer et al. |
| 5,341,818 A | 8/1994 | Abrams et al. |
| 5,342,292 A | 8/1994 | Nita et al. |
| 5,344,395 A | 9/1994 | Whalen et al. |
| 5,346,502 A | 9/1994 | Estabrook et al. |
| 5,362,309 A | 11/1994 | Carter |
| 5,368,557 A | 11/1994 | Nita |
| 5,368,558 A | 11/1994 | Nita et al. |
| 5,376,084 A | 12/1994 | Bacich et al. |
| 5,378,234 A | 1/1995 | Hammerslag et al. |
| 5,380,274 A | 1/1995 | Nita |
| 5,380,316 A | 1/1995 | Aita et al. |
| 5,382,228 A | 1/1995 | Nita et al. |
| 5,383,460 A | 1/1995 | Jang et al. |
| 5,389,096 A | 2/1995 | Aita et al. |
| 5,391,144 A | 2/1995 | Sakurai et al. |
| 5,397,293 A | 3/1995 | Alliger et al. |
| 5,397,301 A | 3/1995 | Pflueger et al. |
| 5,403,324 A | 4/1995 | Ciervo et al. |
| 5,405,318 A | 4/1995 | Nita |
| 5,409,483 A | 4/1995 | Campbell et al. |
| 5,417,672 A | 5/1995 | Nita et al. |
| 5,417,703 A | 5/1995 | Brown et al. |
| 5,421,923 A | 6/1995 | Clarke et al. |
| 5,427,118 A | 6/1995 | Nita et al. |
| 5,431,168 A | 7/1995 | Webster, Jr. |
| 5,431,663 A | 7/1995 | Carter |
| 5,443,078 A | 8/1995 | Uflacker |
| 5,447,509 A | 9/1995 | Mills et al. |
| 5,449,369 A | 9/1995 | Imran |
| 5,449,370 A | 9/1995 | Vaitekunas |
| 5,451,209 A | 9/1995 | Ainsworth et al. |
| 5,462,529 A | 10/1995 | Simpson et al. |
| 5,465,733 A | 11/1995 | Hinohara et al. |
| 5,474,530 A | 12/1995 | Passafaro et al. |
| 5,474,531 A | 12/1995 | Carter |
| 5,480,379 A | 1/1996 | La Rosa |
| 5,484,398 A | 1/1996 | Stoddard |
| 5,487,757 A | 1/1996 | Truckai et al. |
| 5,498,236 A | 3/1996 | Dubrul et al. |
| 5,507,738 A | 4/1996 | Ciervo |
| 5,516,043 A | 5/1996 | Manna et al. |
| 5,527,273 A | 6/1996 | Manna et al. |
| 5,538,512 A | 7/1996 | Zenzon et al. |
| 5,540,656 A | 7/1996 | Pflueger et al. |
| 5,542,917 A | 8/1996 | Nita et al. |
| 5,597,497 A | 1/1997 | Dean et al. |
| 5,597,882 A | 1/1997 | Schiller et al. |
| 5,607,421 A | 3/1997 | Jeevanandam et al. |
| 5,611,807 A | 3/1997 | O'Boyle |
| 5,618,266 A | 4/1997 | Liprie |
| 5,626,593 A | 5/1997 | Imran |
| 5,627,365 A | 5/1997 | Chiba et al. |
| 5,649,935 A | 7/1997 | Kremer et al. |
| 5,658,282 A | 8/1997 | Daw et al. |
| 5,665,062 A * | 9/1997 | Houser .............. A61B 18/1492 604/22 |
| 5,685,841 A | 11/1997 | Mackool |
| 5,695,460 A | 12/1997 | Siegel et al. |
| 5,695,507 A | 12/1997 | Auth et al. |
| 5,715,825 A | 2/1998 | Crowley |

(56) References Cited

U.S. PATENT DOCUMENTS

| | | |
|---|---|---|
| 5,720,724 A | 2/1998 | Ressemann et al. |
| 5,725,494 A | 3/1998 | Brisken |
| 5,728,062 A | 3/1998 | Brisken |
| 5,738,100 A | 4/1998 | Yagami et al. |
| 5,797,876 A | 8/1998 | Spears et al. |
| 5,816,923 A | 10/1998 | Milo et al. |
| 5,827,203 A | 10/1998 | Nita |
| 5,827,971 A | 10/1998 | Hale et al. |
| 5,830,127 A | 11/1998 | DeCastro |
| 5,830,222 A | 11/1998 | Makower |
| 5,846,218 A | 12/1998 | Brisken et al. |
| 5,873,835 A * | 2/1999 | Hastings ............... A61B 5/0215 600/488 |
| 5,876,385 A | 3/1999 | Ikari et al. |
| 5,893,838 A | 4/1999 | Daoud et al. |
| 5,895,397 A | 4/1999 | Jang et al. |
| 5,902,287 A | 5/1999 | Martin |
| 5,904,667 A | 5/1999 | Falwell |
| 5,916,192 A | 6/1999 | Nita et al. |
| 5,916,912 A | 6/1999 | Ames et al. |
| 5,935,142 A | 8/1999 | Hood |
| 5,935,144 A | 8/1999 | Estabrook |
| 5,937,301 A | 8/1999 | Gardner et al. |
| 5,944,737 A | 8/1999 | Tsonton et al. |
| 5,957,882 A | 9/1999 | Nita et al. |
| 5,957,899 A | 9/1999 | Spears et al. |
| 5,964,223 A | 10/1999 | Baran |
| 5,967,984 A | 10/1999 | Chu et al. |
| 5,971,949 A | 10/1999 | Levin et al. |
| 5,976,119 A | 11/1999 | Spears et al. |
| 5,989,208 A | 11/1999 | Nita |
| 5,989,275 A | 11/1999 | Estabrook et al. |
| 5,997,497 A | 12/1999 | Nita et al. |
| 6,004,280 A | 12/1999 | Buck et al. |
| 6,004,335 A | 12/1999 | Vaitekunas et al. |
| 6,007,499 A | 12/1999 | Martin et al. |
| 6,007,514 A | 12/1999 | Nita |
| 6,022,309 A | 2/2000 | Celliers et al. |
| 6,024,764 A | 2/2000 | Schroeppel |
| 6,029,671 A | 2/2000 | Stevens et al. |
| 6,030,357 A | 2/2000 | Daoud et al. |
| 6,036,689 A | 3/2000 | Tu et al. |
| 6,051,010 A | 4/2000 | DiMatteo et al. |
| 6,066,135 A | 5/2000 | Honda |
| 6,113,558 A | 9/2000 | Rosenschein et al. |
| 6,120,515 A * | 9/2000 | Rogers ............ A61B 17/320783 600/467 |
| 6,123,698 A | 9/2000 | Spears et al. |
| 6,142,971 A | 11/2000 | Daoud et al. |
| 6,149,596 A | 11/2000 | Bancroft |
| 6,159,176 A | 12/2000 | Broadwin et al. |
| 6,159,187 A | 12/2000 | Park et al. |
| 6,165,127 A | 12/2000 | Crowley |
| 6,165,188 A | 12/2000 | Saadat et al. |
| 6,179,809 B1 | 1/2001 | Khairkhahan et al. |
| 6,180,059 B1 | 1/2001 | Divino, Jr. et al. |
| 6,190,353 B1 | 2/2001 | Makower et al. |
| 6,206,842 B1 | 3/2001 | Tu et al. |
| 6,210,356 B1 | 4/2001 | Anderson et al. |
| 6,217,543 B1 | 4/2001 | Anis et al. |
| 6,217,565 B1 | 4/2001 | Cohen |
| 6,217,588 B1 | 4/2001 | Jerger et al. |
| 6,221,015 B1 | 4/2001 | Yock |
| 6,231,546 B1 | 5/2001 | Milo et al. |
| 6,231,587 B1 | 5/2001 | Makower |
| 6,235,007 B1 | 5/2001 | Divino, Jr. et al. |
| 6,241,692 B1 | 6/2001 | Tu et al. |
| 6,241,703 B1 | 6/2001 | Levin et al. |
| 6,241,744 B1 | 6/2001 | Imran et al. |
| 6,248,087 B1 | 6/2001 | Spears et al. |
| 6,277,084 B1 | 8/2001 | Abele et al. |
| 6,283,983 B1 | 9/2001 | Makower et al. |
| 6,287,271 B1 | 9/2001 | Dubrul et al. |
| 6,287,285 B1 | 9/2001 | Michal et al. |
| 6,287,317 B1 | 9/2001 | Makower et al. |
| 6,296,620 B1 | 10/2001 | Gesswein et al. |
| 6,298,620 B1 | 10/2001 | Hatzinikolas |
| 6,302,875 B1 | 10/2001 | Makower et al. |
| 6,309,358 B1 | 10/2001 | Okubo |
| 6,315,741 B1 | 11/2001 | Martin et al. |
| 6,315,754 B1 | 11/2001 | Daoud et al. |
| 6,331,171 B1 | 12/2001 | Cohen |
| 6,346,192 B2 | 2/2002 | Buhr et al. |
| 6,379,378 B1 | 4/2002 | Werneth et al. |
| 6,387,109 B1 | 5/2002 | Davison et al. |
| 6,387,324 B1 | 5/2002 | Patterson et al. |
| 6,394,956 B1 | 5/2002 | Chandrasekaran et al. |
| 6,398,736 B1 | 6/2002 | Seward |
| 6,409,673 B2 | 6/2002 | Yock |
| 6,416,533 B1 | 7/2002 | Gobin et al. |
| 6,423,026 B1 | 7/2002 | Gesswein et al. |
| 6,427,118 B1 | 7/2002 | Suzuki |
| 6,433,464 B2 | 8/2002 | Jones |
| 6,434,418 B1 | 8/2002 | Neal et al. |
| 6,450,975 B1 | 9/2002 | Brennan et al. |
| 6,454,737 B1 | 9/2002 | Nita et al. |
| 6,454,757 B1 | 9/2002 | Nita et al. |
| 6,454,997 B1 | 9/2002 | Divino, Jr. et al. |
| 6,484,052 B1 | 11/2002 | Visuri et al. |
| 6,491,707 B2 | 12/2002 | Makower et al. |
| 6,494,891 B1 | 12/2002 | Cornish et al. |
| 6,494,894 B2 | 12/2002 | Mirarchi |
| 6,500,141 B1 | 12/2002 | Irion et al. |
| 6,508,781 B1 | 1/2003 | Brennan et al. |
| 6,508,784 B1 | 1/2003 | Shu |
| 6,511,458 B2 | 1/2003 | Milo et al. |
| 6,514,249 B1 | 2/2003 | Maguire et al. |
| 6,524,251 B2 | 2/2003 | Rabiner et al. |
| 6,533,766 B1 | 3/2003 | Patterson et al. |
| 6,544,215 B1 | 4/2003 | Bencini et al. |
| 6,547,754 B1 | 4/2003 | Evans et al. |
| 6,547,788 B1 | 4/2003 | Maguire et al. |
| 6,551,337 B1 | 4/2003 | Rabiner et al. |
| 6,554,846 B2 | 4/2003 | Hamilton et al. |
| 6,555,059 B1 | 4/2003 | Myrick et al. |
| 6,558,502 B2 | 5/2003 | Divino, Jr. et al. |
| 6,562,031 B2 | 5/2003 | Chandrasekaran et al. |
| 6,573,470 B1 | 6/2003 | Brown et al. |
| 6,576,807 B1 | 6/2003 | Brunelot et al. |
| 6,582,387 B2 | 6/2003 | Derek et al. |
| 6,589,253 B1 | 7/2003 | Cornish et al. |
| 6,595,989 B1 | 7/2003 | Schaer |
| 6,596,235 B2 | 7/2003 | Divino, Jr. et al. |
| 6,602,467 B1 | 8/2003 | Divino, Jr. et al. |
| 6,602,468 B2 | 8/2003 | Patterson et al. |
| 6,605,217 B2 | 8/2003 | Buhr et al. |
| 6,607,698 B1 | 8/2003 | Spears et al. |
| 6,610,077 B1 | 8/2003 | Hancock et al. |
| 6,613,280 B2 | 9/2003 | Myrick et al. |
| 6,615,062 B2 | 9/2003 | Ryan et al. |
| 6,616,617 B1 | 9/2003 | Ferrera et al. |
| 6,622,542 B2 | 9/2003 | Derek et al. |
| 6,623,448 B2 | 9/2003 | Slater |
| 6,635,017 B1 | 10/2003 | Moehring et al. |
| 6,650,923 B1 | 11/2003 | Lesh et al. |
| 6,652,547 B2 | 11/2003 | Rabiner et al. |
| 6,660,013 B2 | 12/2003 | Rabiner et al. |
| 6,676,900 B1 | 1/2004 | Divino, Jr. et al. |
| 6,682,502 B2 | 1/2004 | Bond et al. |
| 6,685,657 B2 | 2/2004 | Jones |
| 6,689,086 B1 | 2/2004 | Nita et al. |
| 6,695,781 B2 | 2/2004 | Rabiner et al. |
| 6,695,782 B2 | 2/2004 | Ranucci et al. |
| 6,695,810 B2 | 2/2004 | Peacock, III et al. |
| 6,702,748 B1 | 3/2004 | Nita et al. |
| 6,702,750 B2 | 3/2004 | Yock |
| 6,719,715 B2 | 4/2004 | Newman et al. |
| 6,719,725 B2 | 4/2004 | Milo et al. |
| 6,729,334 B1 | 5/2004 | Baran |
| 6,733,451 B2 | 5/2004 | Rabiner et al. |
| 6,758,846 B2 | 7/2004 | Goble et al. |
| 6,761,698 B2 | 7/2004 | Shibata et al. |
| 6,814,727 B2 | 11/2004 | Mansouri-Ruiz |
| 6,855,123 B2 | 2/2005 | Nita |

(56) References Cited

U.S. PATENT DOCUMENTS

| | | |
|---|---|---|
| 6,866,670 B2 | 3/2005 | Rabiner et al. |
| 6,936,025 B1 | 8/2005 | Evans et al. |
| 6,936,056 B2 | 8/2005 | Nash et al. |
| 6,942,620 B2 | 9/2005 | Nita et al. |
| 6,942,677 B2 | 9/2005 | Nita et al. |
| 6,955,680 B2 | 10/2005 | Satou et al. |
| 7,004,173 B2 | 2/2006 | Sparks et al. |
| 7,004,176 B2 | 2/2006 | Lau |
| 7,056,294 B2 | 6/2006 | Khairkhahan et al. |
| 7,131,983 B2 | 11/2006 | Murakami |
| 7,137,963 B2 | 11/2006 | Nita et al. |
| 7,149,587 B2 | 12/2006 | Wardle et al. |
| 7,150,853 B2 | 12/2006 | Lee et al. |
| 7,166,098 B1 | 1/2007 | Steward et al. |
| 7,220,233 B2 | 5/2007 | Nita et al. |
| 7,267,650 B2 | 9/2007 | Chow et al. |
| 7,297,131 B2 | 11/2007 | Nita |
| 7,335,180 B2 * | 2/2008 | Nita ............... A61B 17/22004 600/437 |
| 7,341,569 B2 | 3/2008 | Soltani et al. |
| 7,384,407 B2 | 6/2008 | Rodriguez et al. |
| 7,393,338 B2 | 7/2008 | Nita |
| 7,421,900 B2 | 9/2008 | Karasawa et al. |
| 7,425,198 B2 | 9/2008 | Moehring et al. |
| 7,494,468 B2 | 2/2009 | Rabiner et al. |
| 7,503,895 B2 | 3/2009 | Rabiner et al. |
| 7,540,852 B2 * | 6/2009 | Nita ............... A61B 17/22004 604/22 |
| 7,604,608 B2 | 10/2009 | Nita et al. |
| 7,621,902 B2 | 11/2009 | Nita et al. |
| 7,621,929 B2 | 11/2009 | Nita et al. |
| 7,628,763 B2 | 12/2009 | Noriega et al. |
| 7,648,478 B2 | 1/2010 | Soltani et al. |
| 7,758,510 B2 | 7/2010 | Nita et al. |
| 7,771,358 B2 | 8/2010 | Moehring et al. |
| 7,771,452 B2 | 8/2010 | Pal et al. |
| 7,775,994 B2 | 8/2010 | Lockhart |
| 7,776,025 B2 | 8/2010 | Bobo, Jr. |
| 7,819,013 B2 | 10/2010 | Chan et al. |
| 7,850,623 B2 | 12/2010 | Griffin et al. |
| 7,918,819 B2 | 4/2011 | Karmarkar et al. |
| 7,935,108 B2 | 5/2011 | Baxter et al. |
| 7,938,819 B2 | 5/2011 | Kugler et al. |
| 7,942,809 B2 | 5/2011 | Leban |
| 7,955,293 B2 | 6/2011 | Nita et al. |
| 7,993,308 B2 | 8/2011 | Rule et al. |
| 8,038,693 B2 | 10/2011 | Allen |
| 8,043,251 B2 | 10/2011 | Nita et al. |
| 8,052,607 B2 | 11/2011 | Byrd |
| 8,083,727 B2 | 12/2011 | Kugler et al. |
| 8,133,236 B2 | 3/2012 | Nita |
| 8,152,753 B2 | 4/2012 | Nita et al. |
| 8,172,758 B2 | 5/2012 | Harhen |
| 8,221,343 B2 | 7/2012 | Nita et al. |
| 8,226,566 B2 | 7/2012 | Nita |
| 8,246,643 B2 | 8/2012 | Nita |
| 8,257,378 B1 | 9/2012 | O'connor |
| 8,308,677 B2 | 11/2012 | Nita et al. |
| 8,343,134 B2 | 1/2013 | Kost et al. |
| 8,414,543 B2 | 4/2013 | Mcguckin, Jr. et al. |
| 8,496,669 B2 | 7/2013 | Nita et al. |
| 8,506,519 B2 | 8/2013 | Nita |
| 8,613,700 B2 | 12/2013 | Ueno et al. |
| 8,613,751 B2 | 12/2013 | Nita et al. |
| 8,617,096 B2 | 12/2013 | Nita et al. |
| 8,632,560 B2 | 1/2014 | Pal et al. |
| 8,641,630 B2 | 2/2014 | Nita et al. |
| 8,647,293 B2 | 2/2014 | Nita |
| 8,647,296 B2 | 2/2014 | Moberg et al. |
| 8,663,259 B2 | 3/2014 | Levine et al. |
| 8,668,709 B2 | 3/2014 | Nita et al. |
| 8,690,818 B2 | 4/2014 | Bennett et al. |
| 8,690,819 B2 | 4/2014 | Nita et al. |
| 8,702,595 B2 | 4/2014 | Ueki |
| 8,708,892 B2 | 4/2014 | Sugiyama et al. |
| 8,708,994 B2 | 4/2014 | Pettis et al. |
| 8,725,228 B2 | 5/2014 | Koblish et al. |
| 8,764,700 B2 | 7/2014 | Zhang et al. |
| 8,768,433 B2 | 7/2014 | Jenkins et al. |
| 8,790,291 B2 | 7/2014 | Nita et al. |
| 8,974,446 B2 | 3/2015 | Nguyen et al. |
| 8,978,478 B2 | 3/2015 | Ishioka |
| 9,101,387 B2 | 8/2015 | Plowe et al. |
| 9,107,590 B2 | 8/2015 | Hansmann et al. |
| 9,237,837 B2 | 1/2016 | Omoto et al. |
| 9,265,520 B2 | 2/2016 | Nita |
| 9,282,984 B2 | 3/2016 | Nita |
| 9,314,258 B2 | 4/2016 | Nita et al. |
| 9,381,027 B2 | 7/2016 | Nita et al. |
| 9,421,024 B2 | 8/2016 | Nita et al. |
| 9,433,433 B2 | 9/2016 | Nita et al. |
| 9,603,615 B2 | 3/2017 | Sarge |
| 9,770,250 B2 | 9/2017 | Nita et al. |
| 9,955,994 B2 | 5/2018 | Nita |
| 10,004,520 B2 | 6/2018 | Nita et al. |
| 2002/0022858 A1 | 2/2002 | Demond et al. |
| 2002/0049409 A1 | 4/2002 | Noda et al. |
| 2002/0077550 A1 | 6/2002 | Rabiner et al. |
| 2002/0188276 A1 | 12/2002 | Evans et al. |
| 2002/0189357 A1 | 12/2002 | Lai et al. |
| 2003/0008083 A1 * | 1/2003 | Harhen ............... B29C 51/08 428/34.1 |
| 2003/0009153 A1 | 1/2003 | Brisken et al. |
| 2003/0036705 A1 | 2/2003 | Hare et al. |
| 2003/0040762 A1 | 2/2003 | Dorros et al. |
| 2003/0199817 A1 | 10/2003 | Thompson et al. |
| 2003/0216732 A1 | 11/2003 | Truckai et al. |
| 2003/0225332 A1 | 12/2003 | Okada et al. |
| 2004/0019349 A1 | 1/2004 | Fuimaono et al. |
| 2004/0024393 A1 | 2/2004 | Nita et al. |
| 2004/0054367 A1 | 3/2004 | Teodoro, Jr. et al. |
| 2004/0164030 A1 | 8/2004 | Lowe et al. |
| 2004/0167511 A1 | 8/2004 | Buehlmann et al. |
| 2004/0193033 A1 | 9/2004 | Badehi et al. |
| 2005/0033311 A1 | 2/2005 | Guldfeldt et al. |
| 2005/0149110 A1 | 7/2005 | Wholey et al. |
| 2005/0165388 A1 | 7/2005 | Bhola |
| 2005/0171527 A1 | 8/2005 | Bhola |
| 2005/0228286 A1 | 10/2005 | Messerly et al. |
| 2006/0074441 A1 | 4/2006 | Mcguckin, Jr. et al. |
| 2006/0149169 A1 | 7/2006 | Nunomura et al. |
| 2006/0206039 A1 | 9/2006 | Wilson et al. |
| 2006/0264809 A1 | 11/2006 | Hansmann et al. |
| 2007/0032749 A1 | 2/2007 | Overall et al. |
| 2007/0161945 A1 | 7/2007 | Nita et al. |
| 2007/0167813 A1 * | 7/2007 | Lee ............... A61B 8/12 600/459 |
| 2007/0167824 A1 * | 7/2007 | Lee ............... A61B 8/12 600/463 |
| 2007/0167825 A1 * | 7/2007 | Lee ............... A61B 8/12 600/463 |
| 2007/0178768 A1 | 8/2007 | Harshman et al. |
| 2008/0033284 A1 | 2/2008 | Hauck |
| 2008/0071343 A1 | 3/2008 | Mayberry et al. |
| 2008/0208084 A1 | 8/2008 | Horzewski et al. |
| 2008/0221506 A1 | 9/2008 | Rodriguez et al. |
| 2008/0294037 A1 | 11/2008 | Richter |
| 2009/0017293 A1 | 1/2009 | Arai et al. |
| 2009/0143795 A1 | 6/2009 | Robertson |
| 2010/0004558 A1 | 1/2010 | Frankhouser et al. |
| 2010/0023037 A1 | 1/2010 | Nita et al. |
| 2010/0069854 A1 | 3/2010 | Okoh et al. |
| 2010/0076454 A1 | 3/2010 | Bos |
| 2010/0121144 A1 | 5/2010 | Farhadi |
| 2010/0217306 A1 | 8/2010 | Raabe et al. |
| 2010/0268206 A1 | 10/2010 | Manwaring et al. |
| 2011/0046522 A1 * | 2/2011 | Chan ............... A61B 17/22012 601/2 |
| 2011/0105960 A1 | 5/2011 | Wallace |
| 2011/0130834 A1 | 6/2011 | Wilson et al. |
| 2011/0196399 A1 * | 8/2011 | Robertson ............... A61B 17/22004 606/169 |
| 2011/0196403 A1 * | 8/2011 | Robertson ............... A61B 17/320068 606/169 |

(56) References Cited

U.S. PATENT DOCUMENTS

| | | |
|---|---|---|
| 2011/0237982 A1 | 9/2011 | Wallace |
| 2011/0313328 A1 | 12/2011 | Nita |
| 2012/0010506 A1 | 1/2012 | Ullrich |
| 2012/0109021 A1 | 5/2012 | Hastings et al. |
| 2012/0130475 A1 | 5/2012 | Shaw |
| 2012/0165680 A1* | 6/2012 | Akifumi ............... A61B 8/12 600/466 |
| 2012/0217306 A1 | 8/2012 | Morrill Webb et al. |
| 2012/0238916 A1 | 9/2012 | Nita et al. |
| 2012/0238946 A1 | 9/2012 | Nita et al. |
| 2012/0311844 A1 | 12/2012 | Nita et al. |
| 2012/0330196 A1 | 12/2012 | Nita |
| 2013/0046297 A1 | 2/2013 | Lingeman et al. |
| 2013/0060169 A1 | 3/2013 | Yamada |
| 2013/0331652 A1 | 12/2013 | Okamoto |
| 2013/0338580 A1 | 12/2013 | Yamatani et al. |
| 2014/0005706 A1 | 1/2014 | Gelfand et al. |
| 2014/0012087 A1 | 1/2014 | Omoto |
| 2014/0039491 A1 | 2/2014 | Bakos et al. |
| 2014/0171804 A1 | 6/2014 | Van Hoven |
| 2014/0236118 A1 | 8/2014 | Unser et al. |
| 2014/0243712 A1 | 8/2014 | Humayun et al. |
| 2014/0350401 A1* | 11/2014 | Sinelnikov ............... A61B 8/54 600/439 |
| 2014/0358028 A1 | 12/2014 | Vetter et al. |
| 2014/0358029 A1 | 12/2014 | Vetter et al. |
| 2015/0025544 A1 | 1/2015 | Nita et al. |
| 2015/0073357 A1 | 3/2015 | Bagwell et al. |
| 2015/0105621 A1 | 4/2015 | Farhadi |
| 2015/0105715 A1 | 4/2015 | Pikus et al. |
| 2015/0133918 A1 | 5/2015 | Sachar |
| 2015/0148795 A1 | 5/2015 | Amos et al. |
| 2015/0150571 A1 | 6/2015 | Nita et al. |
| 2015/0157443 A1 | 6/2015 | Hauser et al. |
| 2015/0190660 A1 | 7/2015 | Sarge et al. |
| 2015/0297258 A1 | 10/2015 | Escudero et al. |
| 2015/0359651 A1 | 12/2015 | Wübbeling |
| 2016/0128717 A1 | 5/2016 | Nita |
| 2016/0128767 A1 | 5/2016 | Azamian et al. |
| 2016/0135835 A1 | 5/2016 | Onuma |
| 2016/0183956 A1 | 6/2016 | Nita |
| 2016/0271362 A1 | 9/2016 | Van Liere |
| 2016/0328998 A1 | 11/2016 | Nita et al. |
| 2016/0338722 A1 | 11/2016 | Nita et al. |
| 2016/0367284 A1 | 12/2016 | Nita et al. |
| 2017/0065288 A1 | 3/2017 | Imai et al. |
| 2017/0128090 A1 | 5/2017 | Sarge |
| 2017/0224375 A1 | 8/2017 | Robertson et al. |
| 2017/0265879 A1 | 9/2017 | Washburn, II et al. |
| 2017/0265886 A1 | 9/2017 | Nita et al. |
| 2017/0354428 A1 | 12/2017 | Nita et al. |
| 2018/0042636 A1 | 2/2018 | Nita |
| 2018/0140321 A1 | 5/2018 | Deepa |
| 2018/0168668 A1 | 6/2018 | Zheng |
| 2018/0177515 A1 | 6/2018 | Boyle et al. |
| 2018/0197856 A1 | 7/2018 | Chou et al. |
| 2018/0280005 A1 | 10/2018 | Parmentier |
| 2018/0280044 A1 | 10/2018 | Nita et al. |

FOREIGN PATENT DOCUMENTS

| | | |
|---|---|---|
| DE | 2438648 A1 | 2/1976 |
| DE | 8910040 U1 | 12/1989 |
| DE | 3821836 A1 | 1/1990 |
| DE | 4042435 C2 | 2/1994 |
| DE | 10146011 A1 | 4/2003 |
| EP | 0005719 A1 | 12/1979 |
| EP | 0316789 A2 | 5/1989 |
| EP | 0316796 A2 | 5/1989 |
| EP | 0376562 A2 | 7/1990 |
| EP | 0379156 A2 | 7/1990 |
| EP | 0394583 A2 | 10/1990 |
| EP | 0443256 A1 | 8/1991 |
| EP | 0472368 A2 | 2/1992 |
| EP | 0541249 A2 | 5/1993 |
| EP | 0820728 A2 | 1/1998 |
| EP | 1323481 A2 | 7/2003 |
| GB | 1106957 | 3/1968 |
| JP | H2-7150 U | 10/1988 |
| JP | 01-099547 | 4/1989 |
| JP | 6086822 A | 3/1994 |
| JP | H07500752 A | 1/1995 |
| JP | 7116260 A | 5/1995 |
| JP | 9-503137 | 3/1997 |
| JP | 10-216140 | 8/1998 |
| JP | 2000-291543 | 10/2000 |
| JP | 2001-104356 | 4/2001 |
| JP | 2001-321388 | 11/2001 |
| JP | 2002-186627 | 7/2002 |
| JP | 2005-253874 | 9/2005 |
| JP | 2006-522644 A | 10/2006 |
| JP | 2007512087 A | 5/2007 |
| JP | 2007520255 A | 7/2007 |
| WO | 8705739 A1 | 9/1987 |
| WO | 8705793 A1 | 10/1987 |
| WO | 8906515 A1 | 7/1989 |
| WO | 9001300 A1 | 2/1990 |
| WO | 9004362 A1 | 5/1990 |
| WO | 9107917 A2 | 6/1991 |
| WO | 9211815 A2 | 7/1992 |
| WO | 9308750 A2 | 5/1993 |
| WO | 9316646 A1 | 9/1993 |
| WO | 9412140 A1 | 6/1994 |
| WO | 9414382 A1 | 7/1994 |
| WO | 9508954 A1 | 4/1995 |
| WO | 9509571 A1 | 4/1995 |
| WO | 9515192 A1 | 6/1995 |
| WO | 9635469 A1 | 11/1996 |
| WO | 9705739 A1 | 2/1997 |
| WO | 9721462 A1 | 6/1997 |
| WO | 9745078 A1 | 12/1997 |
| WO | 9827874 A1 | 7/1998 |
| WO | 9835721 A2 | 8/1998 |
| WO | 9851224 A2 | 11/1998 |
| WO | 9852637 A1 | 11/1998 |
| WO | 9925412 A2 | 5/1999 |
| WO | 0053341 A1 | 9/2000 |
| WO | 0067830 A1 | 11/2000 |
| WO | WO02094103 A1 | 11/2002 |
| WO | 03039381 A1 | 5/2003 |
| WO | 2004012609 A1 | 2/2004 |
| WO | 2004093736 A2 | 11/2004 |
| WO | 2004112888 A2 | 12/2004 |
| WO | 2005053769 A2 | 6/2005 |
| WO | 2005112770 A1 | 12/2005 |
| WO | 2006049593 A1 | 5/2006 |
| WO | 2013109269 A1 | 7/2013 |
| WO | 2014022716 A2 | 2/2014 |
| WO | 2014105754 A1 | 7/2014 |
| WO | 2014106847 A1 | 7/2014 |
| WO | 2018097856 A1 | 5/2018 |
| WO | 20180187159 A1 | 10/2018 |

OTHER PUBLICATIONS

Definition of the term "connected", retrieved on Sep. 21, 2013. <www.thefreedictionary.com/connected> 1 page total.

Supplemental European Search Report dated Nov. 5, 2009 for European Application No. EP03766931.

International Search Report dated Oct. 28, 2003 for PCT Application No. PCT/US2003/023468.

Extended European Search Report dated Mar. 22, 2012 for European Application No. EP11188799.

International Search Report dated Dec. 23, 2005 for PCT Application No. PCT/US2004/019378.

Extended European Search Report for Patent Application No. 06718204.8, dated May 30, 2012.

International Search Report dated Aug. 1, 2013 for PCT Application No. PCT/US2013/053306.

International Preliminary Report dated Aug. 1, 2013 for PCT Application No. PCT/US2013/053306.

(56) References Cited

OTHER PUBLICATIONS

Written Opinion dated Aug. 1, 2013 for PCT Application No. PCT/US2013/053306.
Supplemental European Search Report dated Apr. 29, 2009 for European Application No. EP 04711207.3.
Office Action dated Aug. 3, 2010 from Japanese Application No. 2006-517355 filed on Jun. 16, 2004.
Office Action dated Jan. 26, 2010 from Japanese Application No. 2006-517355 filed on Jun. 16, 2004.
International Preliminary Report and Written Opinion dated Aug. 1, 2017 for PCT Application No. PCT/US2017/030675.
International Preliminary Report and Written Opinion dated Feb. 6, 2018 for PCT Application No. PCT/US2018/017022.
Calhoun et al., "Electron-Beam Systems for Medical Device Sterilization", downloaded from web on Oct. 8, 2002 <http://www.devicelink.com/mpb/archive/97/07/002.html> 7 pages total.
Definition of the term "coupled", retrieved on May 18, 2013. <http://www.merriam-webster.com/dictionary/couple> 1 page total.
"E-Beam Theory" RDI-IBA Technology Group, downloaded from web on Oct. 8, 2002 <http://www.e-beamrdi/EbeamTheory.htm> 2 pages total.
Office Action dated May 20, 2010 from Japanese Application No. 2006-541200 filed on Oct. 25, 2004.
Office Action dated Oct. 11, 2012 from Japanese Application No. 2010-181956.
Extended European Search Report dated Mar. 5, 2012 for European Application No. 12153606.4-1269.
Margaret Fyfe et al., Mast cell degranulation and increased vascular permeability induced by therapeutic ultrasound in the rate ankle joint, Br. J. exp. Path., 1984, vol. 65, pp. 671-676.
"Irradiation, Biological, and Other Technologies: E-beam, Biological, and Sharps Treatment Systems", Non-ncineration Medical Waste Treatment Technologies, Aug. 2001, Chapter 9, pp. 69-74, Health Care Without Harm, Washington, DC.
Paul Yock et al., Catheter-Based Ultrasound Thrombolysis Shake, Rattle, and Repertuse, https://doi.org/10.1161/01.CIR.95.6.1360 Circulation. 1997;95:1360-1362 Originally published Mar. 18, 1997.
Japanese Office Action for Japanese Application No. 2010-134566, dated Mar. 2, 2012.
Sehgal, et al., Ultrasound-Assisted Thrombolysis, Investigative Radiology, 1993, vol. 28, Issue 10, pp. 939-943.
Siegel, et al., "In Vivo Ultrasound Arterial Recanalization of Atherosclerotic Total Occlusions", Journal of the American College of Cardiology, Feb. 1990, vol. 15, No. 2, pp. 345-351.
"What is Electron Beam Curing?" downloaded from web on Nov. 14, 2002, 4 pages total. <http://www.ms.oml.gov/researchgroups/composites/new%20orccmt%20pages/pages/ebwha>.
EP Extended Search Report dated Aug. 13, 2009; Application 04710537.5-1269, 5 pages.

\* cited by examiner

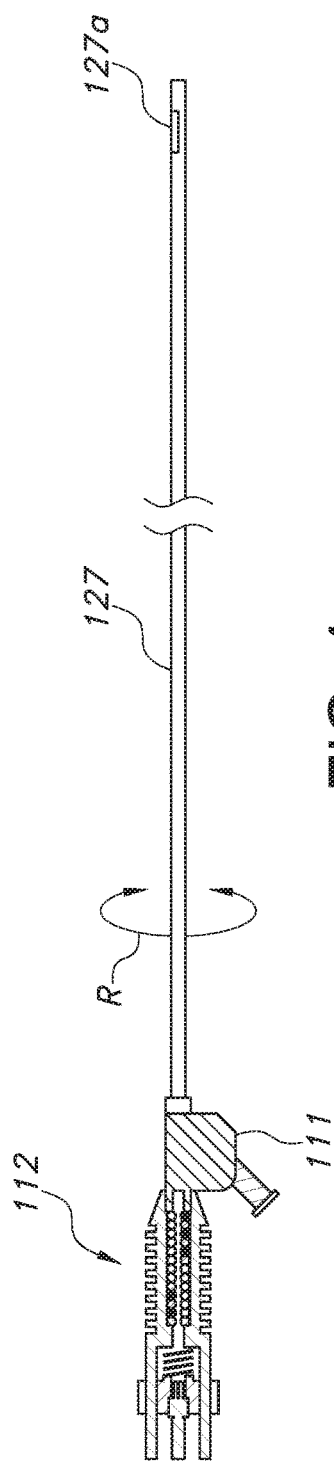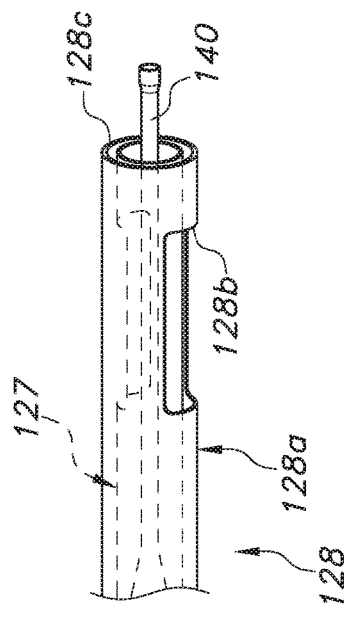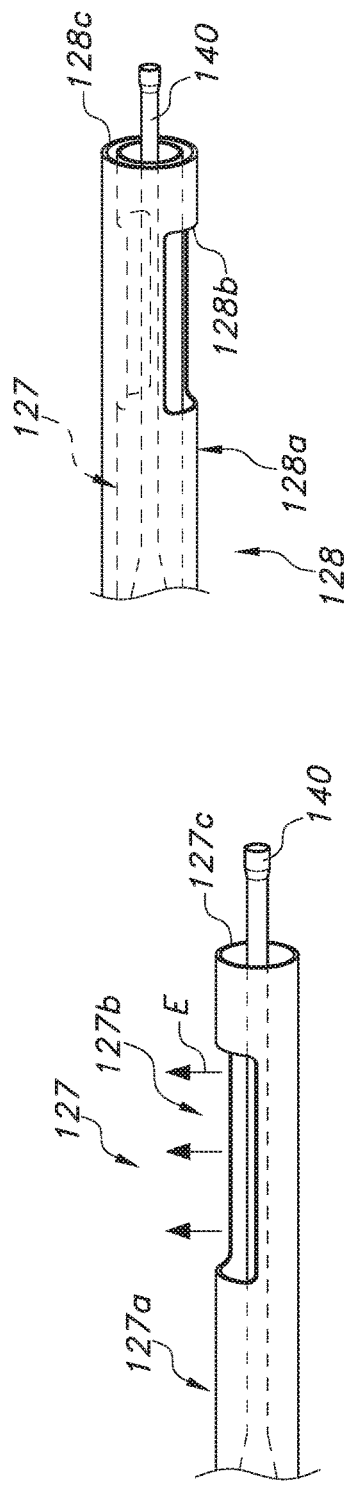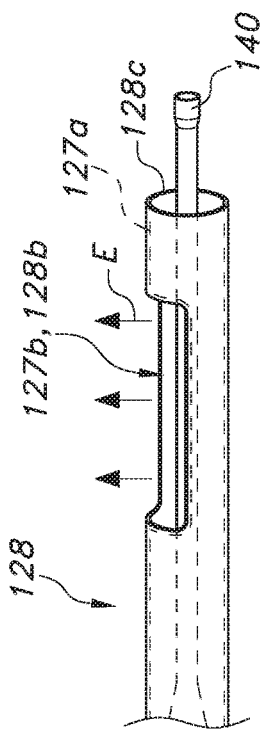
FIG. 4
FIG. 6
FIG. 5
FIG. 7

US 10,582,983 B2

ULTRASONIC ENDOVASCULAR CATHETER WITH A CONTROLLABLE SHEATH

TECHNICAL FIELD

This document relates generally to the art of endovascular procedures and, more particularly, to an endovascular catheter using ultrasonic energy to perform a medical procedure, such as an atherectomy or crossing an occlusion, using a controllable sheath.

BACKGROUND

Ultrasonic catheters have been proposed. An example of such a catheter is shown in U.S. Pat. No. 7,540,852, the disclosure of which is fully incorporated herein by reference. While this catheter achieves the desired result of providing enhanced disruption of blood vessel obstructions, the present disclosure proposes certain modifications or improvements to enhance the results achieved during an endovascular procedure in terms of clearing an obstruction from a vessel (such as, for example, an atherectomy for removing atherosclerosis from a blood vessel, or for crossing an occlusion).

SUMMARY

According to a first aspect of the disclosure, an apparatus for performing an endovascular procedure using ultrasonic energy. The apparatus comprises a catheter including a proximal end portion and a distal end portion having a first window, which may be elongated in a longitudinal direction of the catheter. A wave guide is provided for delivering the ultrasonic energy for performing the endovascular procedure. A cover is also provided for selectively covering the window.

In one embodiment, the distal end portion of the catheter includes an opening through which the wave guide may pass. The catheter may comprise a first sheath including the first window. The cover may comprise a rotatable second sheath for covering the first window of the first sheath. The second sheath may include a second window for aligning with the first window, as well as an opening through which the wave guide may pass.

According to a further aspect of the disclosure, an apparatus for performing an endovascular procedure is provided. The apparatus includes a source of ultrasonic energy, and a wave guide for delivering the ultrasonic energy for performing the endovascular procedure. A catheter is provided for receiving the wave guide. The catheter includes a first window for transmitting ultrasonic energy from the wave guide and an opening at a distal end through which the wave guide may pass.

In one embodiment, a cover is provided for selectively covering the first window, which may be elongated in a longitudinal direction of the catheter. The catheter may comprise a first sheath including the window, and the cover may comprise a rotatable second sheath for covering the window of the first sheath. The second sheath may include a second window for aligning with the window of the first sheath. The second sheath may further include an opening through which the wave guide may pass.

Still a further aspect of the disclosure pertains to an apparatus for performing an endovascular procedure using ultrasonic energy. The apparatus comprises a wave guide for delivering the ultrasonic energy for performing the endovascular procedure. A catheter is adapted for selectively blocking or transmitting the ultrasonic energy from the wave guide.

In one embodiment, the catheter comprises a first window for exposing a portion of the wave guide. A cover is also provided for covering the first window. The catheter may comprise a first sheath including the first window and a second sheath forming the cover. The second sheath may also comprise a second window corresponding to the first window. One or both of the first and second sheaths may be rotatably mounted to the catheter. A source connected to the catheter may supply ultrasonic energy to the wave guide.

BRIEF DESCRIPTION OF THE DRAWING FIGURES

The accompanying drawing figures incorporated herein and forming a part of the specification, illustrate several aspects of the ultrasonic endovascular catheter with a controllable sheath and, together with the description, serve to explain certain principles thereof. In the drawing figures:

FIG. 4 is a side view of a catheter with a controllable sheath according to one aspect of the disclosure;

FIG. 5 is a close-up view of the distal end portion of the catheter of FIG. 4; and FIGS. 6 and 7 illustrate an alternate embodiment.

Reference will now be made in detail to the presently disclosed embodiments of the inventive aspects of the ultrasonic endovascular catheter with a controllable sheath, examples of which are illustrated in the accompanying drawing figures.

DETAILED DESCRIPTION

Ultrasound or ultrasonic catheters provide for disruption of occlusions in blood vessels, such as for example, plaques, clots, lesions, or like objects that hinder blood flow. Catheters generally include a catheter body (shaft), an ultrasonic energy transmission member disposed within the catheter body and a distal head coupled with the energy transmission member and disposed at or near the distal end of the catheter body. The ultrasonic wave guide transmits ultrasonic energy from an ultrasonic transducer to the distal end of the catheter, causing it to vibrate and, thus, disrupt, dissolve, or debulk vascular occlusions (which procedures are generally called atherectomies or thrombectomies). A number of improved features of such an ultrasonic catheter are outlined more fully in the following description.

Figure 1:
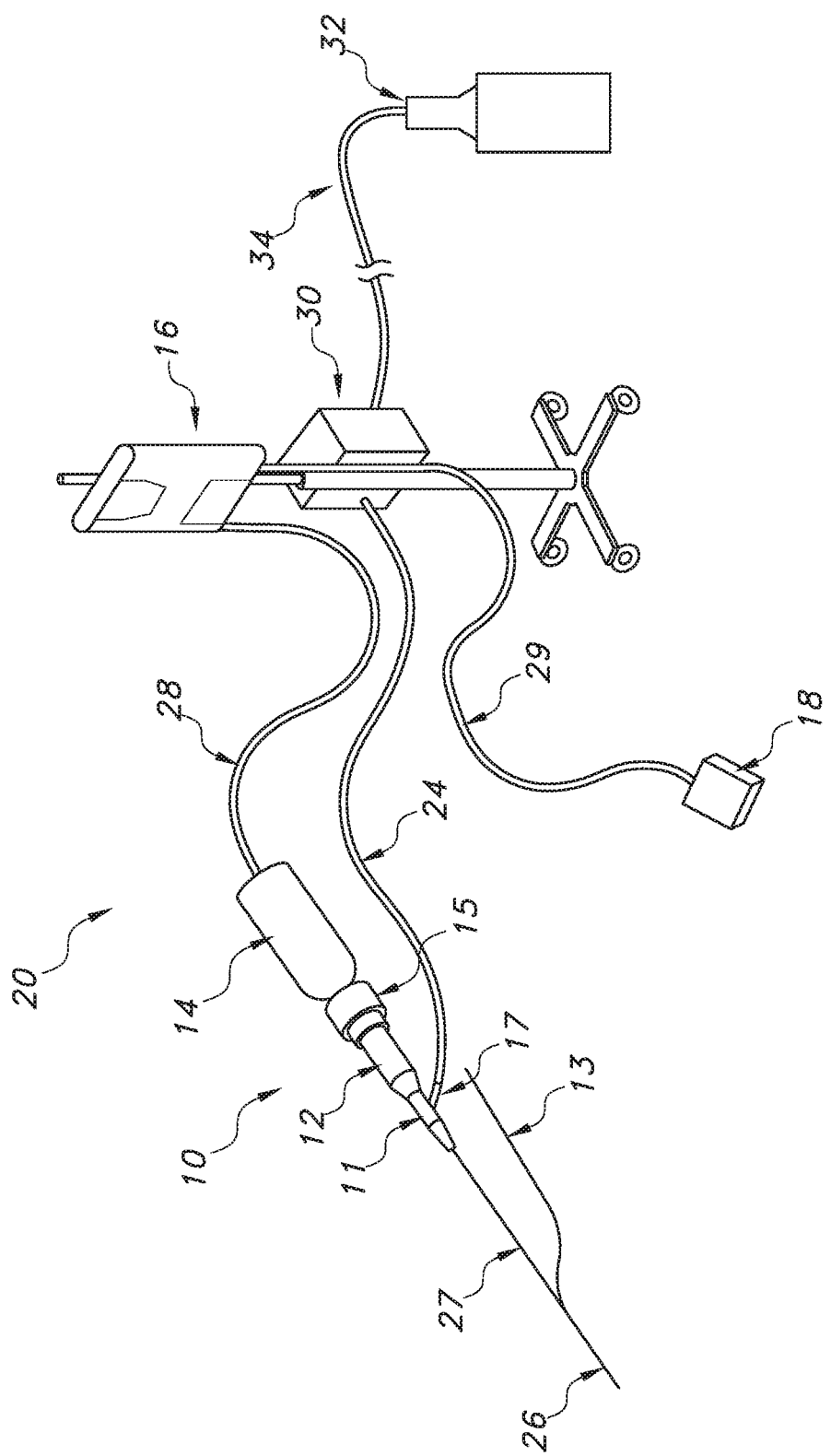
FIG. 1 is a schematic view of a prior art catheter system including an ultrasonic catheter.

Referring now to FIG. 1, one embodiment of an ultrasonic catheter system 20 includes an ultrasound or ultrasonic catheter 10 and an energy source 16 (which may comprise an ultrasonic generator). Catheter 10 includes a distal end 26 for disrupting occlusions, a catheter shaft or body 27, and a proximal connector 12 for coupling catheter 10 with an ultrasonic transducer 14. Ultrasonic transducer 14 is coupled with source 16 via a connector 28, and generator is coupled with a control, such as a foot-actuated on/off switch 18 via another connector 29. Source 16 provides energy to transducer 14 and, thus, to ultrasonic catheter 10.

Catheter 10 further includes an ultrasonic wave guide (or "core wire"—not shown in FIG. 1) that extends through the catheter body 27 and transmits energy from the transducer 14 to the distal end 26. Some embodiments of catheter 10 include a guidewire, which in FIG. 1 is shown as a so-called "rapid exchange" guidewire 13 and guidewire port, while other embodiments include a proximal guidewire port for over the wire guidewire delivery. In some embodiments, transducer 14 further includes a coupler 15 for coupling the catheter 10 to transducer 14. Connectors 28, 29 may comprise an electric cord or cable or any other suitable connecting devices for coupling on/off switch 18, source 16 and transducer 14. In an alternative embodiment, on/off switch 18 is located on source 16.

In addition to proximal connector 12, ultrasonic catheter 10 may include one or more other various components, such as a Y-connector 11 including a fluid inlet port 17 (or aperture) for passage of irrigation fluid. Inlet port 17 may be removably coupled with an irrigation tube 24, which in one embodiment may be coupled with a fluid refrigerator 30. The refrigerator 30 may, in turn, be coupled with a fluid container 32 via a connector tube 34. This arrangement may be used for introducing one or more fluids into catheter 10. Fluid may be used to cool any part of the device, such as the ultrasonic wave guide, thus helping reduce wear and tear on the catheter 10. In some embodiments, fluid inlet port 17 is located farther proximally on proximal connector 12, to allow fluid to be applied within connector 12. In some embodiments, refrigerated fluid is used, while in other embodiments irrigation fluid may be kept at room temperature. In various embodiments, oxygen supersaturated fluid, lubricious fluid, or any other suitable fluid or combination of fluids may be used, and again, such fluids may be refrigerated or kept room temperature. In an alternative embodiment to that shown in FIG. 1, refrigerator 30 and fluid container 32 are combined in one unit.

Generally, catheter 10 may include any suitable number of side-arms or ports for passage of a guidewire, application of suction, infusing and/or withdrawing irrigation fluid, dye and/or the like, or any other suitable ports or connections. Also, ultrasonic catheters 10 per the disclosure may be used with any suitable proximal devices, such as any suitable ultrasonic transducer 14, energy source 16, coupling device (s) and/or the like. Therefore, the exemplary embodiment shown in FIG. 1 and any following descriptions of proximal apparatus or systems for use with ultrasonic catheters 10 should not be interpreted to limit the scope of the appended claims.

Figure 2:
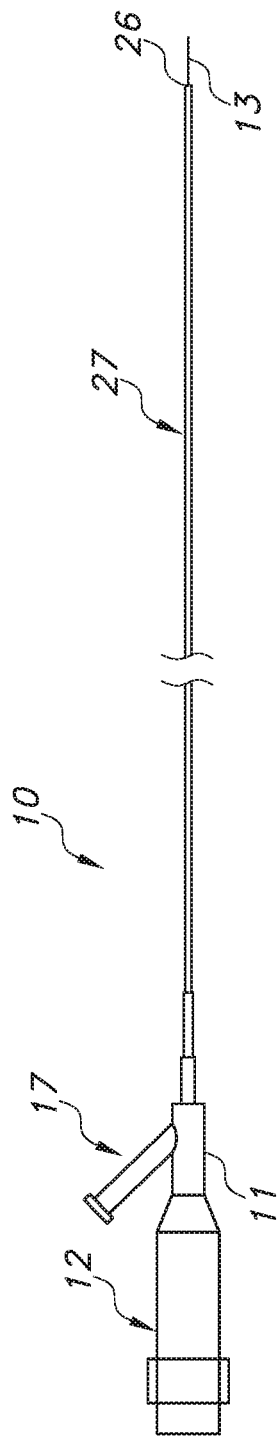
FIG. 2 is a side view illustrating a general layout of a prior art catheter.

Referring now to FIG. 2, an enlarged view of catheter 10 is shown. Proximal connector 12, Y-connector 11, inlet port 17, catheter body 27, distal end 26 and guidewire 13 are all shown. Catheter body 27 is generally a flexible, tubular, elongate member, having any suitable diameter and length for reaching a vascular occlusion for treatment. In one embodiment, for example, catheter body 27 preferably has an outer diameter of between about 0.5 mm and about 5.0 mm. In other embodiments, as in catheters intended for use in relatively small vessels, catheter body 27 may have an outer diameter of between about 0.25 mm and about 2.5 mm. Catheter body 27 may also have any suitable length. As discussed briefly above, for example, some ultrasonic catheters have a length in the range of about 150 cm. However, any other suitable length may be used without departing from the scope of the present disclosure.

Figure 3:
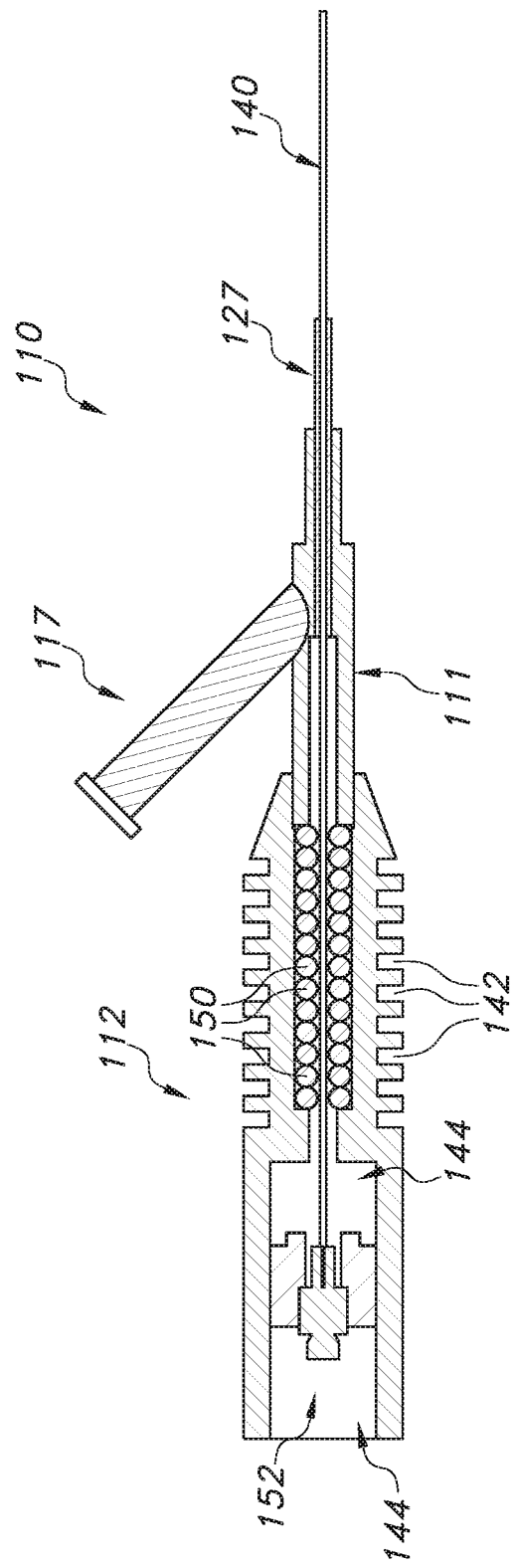
FIG. 3 is a partially cross-sectional, partially cutaway view of a catheter including an ultrasonic wave guide.

Referring now to FIG. 3, a proximal portion of one embodiment of an ultrasonic catheter 110 is shown in cross-section. An ultrasonic wave guide 140 extends from a sonic connector 152 distally to a distal end (not shown) of catheter 110. A catheter body 127 of catheter 110 is shown only in part in this Figure, whereas catheter body may extend distally to (or near) the distal end of catheter 110, as shown in FIG. 4, with the wave guide 140 also extending a particularly long distance (e.g., 30 centimeters or greater, and typically between about 15 centimeters and 30 centimeters). The catheter body 127 may be a constant diameter, or may have a variable diameter from the proximal to the distal end (such as, for example, wider in diameter at the proximal end near the point of entering the vasculature than at the distal end).

Catheter 110 also includes a proximal housing 112 (or "proximal connector"), having an inner bore 144 (or "inner cavity") in which sonic connector 152, a portion of ultrasonic wave guide 140 and one or more vibration absorbers 150 reside. Housing 112 is coupled with a Y-connector 111, which includes a fluid inlet port 117 (or aperture), and Y-connector 111 is coupled with catheter body 127.

In various embodiments, housing 112 may suitably include one or more surface features 142 for increasing the overall surface area of the outer surface of housing 112. Increased surface area enhances the ability of housing 112 to dissipate heat generated by ultrasonic wave guide 140 out of catheter 110. Surface features 142 may have any suitable size or shape, such as ridges, jags, undulations, grooves or the like, and any suitable number of surface features 142 may be used. Additionally, housing 112 may be made of one or more heat dissipating materials, such as aluminum, stainless steel, any other conductive metal(s), or any suitable non-metallic conductive material(s).

In most embodiments, ultrasonic wave guide 140, such as wire, extends longitudinally through a lumen of catheter body 127 to transmit ultrasonic energy from an ultrasonic transducer 14 (not shown in FIGS. 2 and 3), connected to the proximal end of proximal housing 112, to the distal end of catheter 110. Wave guide 140 may be formed of any material capable of effectively transmitting ultrasonic energy from the ultrasonic transducer 14 to the distal end of catheter body 127, including but not limited to metals such as pure titanium or aluminum, titanium or aluminum alloys, or shape memory materials (such as nitinol), and may be coated (such as using a polymeric material). Again, additional details of ultrasonic wave guides 140 may be found in the patent applications incorporated by reference. Similarly, reference may be made to the incorporated references for descriptions of housing 112, sonic connector 152, vibration absorbers 150, Y-connector 111 and the like. For example, housing 112 and other features are described in U.S. Pat. No. 7,335,180, the disclosure of which is incorporated herein by reference.

Ultrasonic wave guide 140 typically passes from a sonic connector 152, through bore 144 and Y-connector 111, and then through catheter body 127. Fluid inlet port 117 is in fluid communication with a lumen in Y-connector, which is in fluid communication with a lumen extending through catheter body 127. Thus, fluid introduced into fluid inlet port 117 is typically free to flow into and through catheter body 127 to contact ultrasonic wave guide 140. Fluid may flow out of catheter body 127 through apertures in the distal head (not shown) or through any other suitable apertures or openings, such as apertures located in catheter body 127 itself. Any suitable fluid may be passed through fluid inlet port 117 and catheter body 127, such as refrigerated fluid, lubricious fluid, super-saturated saline or contrast/saline mixture, or the like. Cooling and/or lubricating ultrasonic wave guide 140 may reduce friction and/or wear and tear of ultrasonic wave guide 140, thus prolonging the useful life of ultrasonic catheter 110 and enhancing its performance.

Referring now to FIG. 4, it can be understood that the catheter body 127 may take the form of a sheath 127a in which the wave guide 140 is at least partially positioned. The proximal end of the sheath 127a may be positioned adjacent to the housing 112, and may extend within the Y-connector 111, as shown in FIG. 3, or may be external to it, as shown in FIG. 4. In either case, the sheath 127a may be adapted to rotate relative to the wave guide 140, as indicated by action arrow R. Alternatively, the sheath 127a may be fixed in position relative to the connector 111 or housing 112.

The sheath 127a may also include a lateral or side opening, such as a window 127b, adjacent to a portion of the wave guide 140, and thus exposing it to the interior of a lumen or vessel when positioned therein. As indicated in FIG. 5, the sheath 127a may be rotated relative to the wave guide 140, such that the direction of the ultrasonic energy is controlled by the position of the window 127b (note action arrows E) or, alternatively, the entire catheter 110 may be rotated if the sheath is fixed. In either case, by selectively controlling the position of the window 127b through rotation, a focused or targeted treatment may be provided for a particular area of the vessel in which the catheter 110 is at least partially positioned, since only a portion of the wave guide 140 is exposed to the opening thus formed.

To allow for an enhanced level of control, the window 127b may also be selectively blocked. This may be achieved by providing a cover 128 for selectively covering the opening or window 127b in the sheath 127a. As indicated in FIGS. 6 and 7, the cover 128 may comprise a second sheath 128a over the first sheath 127a, such that the two structures are generally concentric about the wave guide 140. This second sheath 127a may also extend to the proximal end of the catheter 110, such as adjacent to or within the connector 111, and may include an open end 128c. The second sheath 128a may further include a lateral or side opening, such as a window 128b, which may have a size and shape matching or corresponding to window 127b in the first sheath 127a.

Thus, as indicated in FIG. 6, the second sheath 128a may be rotated relative to the first sheath 127a (which may be fixed or stationary, or also rotatable as noted above) such that the window 127b is covered by a portion of the second sheath. In this manner, the energy may be directed to wave guide 140 through the open end 127c of the sheaths 127a, 128a, and the catheter 110 may be used in crossing a chronic total occlusion (CTO) in this configuration.

When it is desired to allow for ultrasonic energy to be transmitted radially of the longitudinal axis of the catheter 110, the second sheath 128a may be rotated to align the windows 127b, 128b. This allows the energy (arrow E) to pass into the vessel through the opening thus formed, as shown in FIG. 7. The relative rotation may also be achieved such that the opening only partially exposes the wave guide 140, which may provide for a further level of control.

Control of the relative rotation may be achieved at the proximal end of the catheter by providing suitable markings on the sheaths 127a, 128a to indicate the aligned position of the openings or windows 127b, 128b. The markings may be in the form of printed indicia, but may also take the form of bosses or embosses (and may be arranged to interact to create a temporary locked condition). Alternatively, radiographic visualization may be used, such as by providing one or more radiopaque markers on the periphery of the windows 127b, 128b. Alignment of the markers under fluoroscopy may indicate the aligned position of the windows.

In summary, an improved ultrasonic catheter 110 includes a controllable sheath 127a or 128a. One or both of the sheaths 127a, 128a may include windows 127b, 128b and may be adapted for relative rotation. By aligning the windows 127b, 128b to form an opening, the transmission of energy from a wave guide 140 associated with the catheter 110 may result. Yet, the catheter 110 may also be used in a "crossing" mode, such as for crossing a CTO, by reorienting the sheaths 127a, 128a and thus closing the opening formed by the windows 127b, 128b and regulating the transmission of ultrasonic energy.

The foregoing description has been presented for purposes of illustration. It is not intended to be exhaustive or to limit the embodiments to the precise form disclosed. Obvious modifications and variations are possible in light of the above teachings. For instance, instead of rotatable sheaths 127a, 128a, one or both of the sheaths may be made to telescope relative to each other to selectively uncover or block the opening for transmitting energy radially from the wave guide 140. The size and shape of the opening formed by the window 127b or 128b may also be altered from what is shown in the drawings to suit a particular desire or need in terms of a treatment regimen. All modifications and variations are within the scope of the appended claims when interpreted in accordance with the breadth to which they are fairly, legally and equitably entitled.

What is claimed:

1. An apparatus for performing an endovascular procedure using ultrasonic energy, comprising:
   a catheter including a proximal end portion and a distal end portion, the distal end portion having a first window;
   a wave guide positioned in the catheter for delivering the ultrasonic energy through the first window for performing the endovascular procedure; and
   a cover for selectively covering the first window,
   wherein the catheter comprises a first sheath including the first window, and the cover comprises a rotatable second sheath for selectively covering the first window of the first sheath.

2. The apparatus of claim 1, wherein the distal end portion of the catheter includes an opening through which the wave guide may pass.

3. The apparatus of claim 1, wherein the second sheath includes a second window for aligning with the first window.

4. The apparatus of claim 1, wherein the second sheath includes an opening through which the wave guide may pass.

5. The apparatus of claim 1, wherein the first window is elongated in a longitudinal direction of the catheter.

6. An apparatus for performing an endovascular procedure, comprising:
   a source of ultrasonic energy;
   a wave guide for delivering the ultrasonic energy for performing the endovascular procedure; and
   a catheter for receiving the wave guide, the catheter including a first sheath including a first window, and a cover comprises a movable second sheath for selectively blocking or covering the first window of the first sheath.

7. The apparatus of claim 6, wherein the second sheath includes a second window for aligning with the first window of the first sheath.

8. The apparatus of claim 6, wherein the second sheath includes an opening through which the wave guide may pass.

9. The apparatus of claim 6, wherein the window is elongated in a longitudinal direction of the catheter.

10. An apparatus for performing an endovascular procedure using ultrasonic energy, comprising:

a wave guide for delivering the ultrasonic energy for performing the endovascular procedure, the wave guide including a distal end;

a catheter that receives the wave guide, the catheter having a first window for exposing a portion of the wave guide, and the catheter having a cover at least partially covering the first window and adapted for selectively blocking or transmitting the ultrasonic energy at the first window; and a source connected to the catheter for supplying ultrasonic energy to the wave guide.

11. The apparatus of claim 10, wherein the catheter comprises a first sheath including the first window and a second sheath forming the cover.

12. The apparatus of claim 11, wherein the second sheath comprises a second window corresponding to the first window.

13. The apparatus of claim 12, wherein the first sheath is rotatably mounted to the catheter, wherein the first window is rotationally misaligned with the second window to cover the first window.

14. The apparatus of claim 12, wherein the second sheath is rotatably mounted to the catheter, wherein the second window is rotationally misaligned with the first window to cover the first window.

* * * * *